United States Patent [19]

Roberts et al.

[11] Patent Number: 4,584,729

[45] Date of Patent: Apr. 29, 1986

[54] DISPOSABLE FULL SPINAL IMMOBILIZATION BACKBOARD

[76] Inventors: Jess D. Roberts, 12875 Tibarand Dr.; George E. Wimpelberg, 1600 Fleener Ct., both of Evansville, Ind. 47711

[21] Appl. No.: 602,603

[22] Filed: Apr. 20, 1984

[51] Int. Cl.[4] ........................... A61G 1/00; A61F 5/04

[52] U.S. Cl. .................................... 5/82 R; 5/DIG. 1; 128/88; 128/87 R

[58] Field of Search ................ 5/81 R, 82 R, DIG. 1; 128/87 R, 87 B, 87 C, 88, 133, 134; 428/184, 186; 108/51.3

[56] References Cited

U.S. PATENT DOCUMENTS

| | | | |
|---|---|---|---|
| 2,409,195 | 10/1946 | Crawford | 128/87 |
| 2,744,713 | 5/1956 | De Villers | 108/51.3 |
| 2,870,461 | 1/1959 | Rosenthal | 5/93 R |
| 3,151,343 | 10/1964 | McCormick | 5/82 R |
| 3,273,518 | 9/1966 | Shine | 108/51.3 |
| 3,487,479 | 1/1970 | Grooms | 5/99 R |
| 3,496,934 | 2/1970 | Anderson | 128/88 |
| 3,624,745 | 11/1971 | Bowers | 128/87 R |
| 4,209,011 | 6/1980 | Peck | 128/87 R |
| 4,383,526 | 5/1983 | Robins | 128/87 R |
| 4,424,753 | 1/1984 | Eatherton | 428/186 |

*Primary Examiner*—Kenneth J. Dorner
*Assistant Examiner*—Michael F. Trettel
*Attorney, Agent, or Firm*—Woodard, Weikart, Emhardt & Naughton

[57] ABSTRACT

A disposable total spinal immobilization backboard of multiple ply corrugated material impregnated with a waxing substance by a cascading process which acts to both waterproof and to improve the strength and rigidity of the backboard. A panel has a width of about 16 inches and a length of about 6 feet and is reinforced to allow a deflection of less than ½ inch either laterally or longitudinally when exposed to a weight of 300 pounds. Handholds receive hands for the carrying of an injured party. An injured party is securely strapped to strap receiving means, including handholds whereby total spinal immobilization is effectuated for safe and secure transfer.

6 Claims, 6 Drawing Figures

DISPOSABLE FULL SPINAL IMMOBILIZATION BACKBOARD

BACKGROUND OF THE INVENTION

1. Field of the Invention

This invention generally relates to medical emergency rescue equipment. More specifically, this invention relates to such particular equipment referred to as spinal immobilization devices.

2. Brief Description of the Prior Art

Various types of apparatus have been used in the transport of injured people from a casualty area to a place where they can receive required medical attention. The equipment applied to the effectuating of such transfers may vary widely depending upon the particular circumstances involved. Where the injury is slight, a victim may need little or no assistance in bringing himself to a place where medical attention is available. However, where the injury is severe or uncertain, or where reaching the point of treatment is not totally straightforward, the utmost of care should be given in the transport of the injured party.

Often when assistance is indicated, the transfer is accomplished with the use of a stretcher or litter. The injured party is simply placed on the stretcher or litter, usually in a supine position, and carried to an ambulance or a point where further medical attention may be given. A typical such device would include a piece of canvas to which is attached two oppositely positioned poles running longitudinally along the length of the canvas. The patient lies on the canvas between the poles and is carried by two people who grip the stretcher by holding the ends of the poles.

Where there is any possibility whatsoever that there may have been an injury to the spine, however, the use of any simple stretcher or litter which does not completely immobilize the injured party is dangerous and ill advised. In such situations, it is imperative that the total body be maintained in as exactly the same position as possible until such time as the exact extent of the injury is ascertained. Any allowed movement prior to a thorough examination and diagnosis by an attending physician may result in paralysis or death. Because of the prospect of such a disastrous occurrence where total immobilization is not imposed, any indicated transfer of an unconscious or severely injured person includes immobilization.

Where the injured person is found in a lying position, this immobilization is accomplished by means of a spinal immobilization backboard. Such boards are full length boards (typically 6 feet long) and are sized (16 inches) to be narrower than the width of a typical person. The injured party is carefully placed on the board in the position he is found, and then tightly bound to the board with the use of straps to immobilize him to that position. The rigidity of the board essentially freezes the injury through transport and until full medical attention can be given. Since maintaining the rigidity of the board is of extreme importance, even when under the weight of a heavy person, spinal immobilization boards are typically made of hard wood material or metal. These boards are maintained as standard equipment on ambulances in compartments specially sized to receive them.

Where the injured person is found in other than a lying position (such as in the seat of an automobile) a "short board" may be used prior to immobilizing the person to a full spinal immobilization backboard. "Short boards" are typically only 3 feet in length and 14 inches in width. They also include a narrower portion at one end (8 inches) which is sized for binding to the head of a person. To extricate the injured party with minimal risk of aggravating an injury to the spine, a short board is placed behind the person and tightly bound to him. This procedure freezes the position of the neck in relation to the back as best as the circumstances allow until he can be positioned on, and strapped to, a full backboard. Short boards are also made of hard wood material or metal to ensure their rigidity.

SUMMARY OF THE INVENTION

Since total spinal immobilization backboards commonly avoid the aggravation of injuries which would otherwise occur where non-immobilizing devices (such as stretchers) are used, these backboards have become generally accepted in the medical rescue profession. They have become standard equipment on most emergency medical vehicles and are the conveyance means of choice in many rescue situations.

Because of the extreme precautions which are attendant with the transfer of any severely injured or unconscious patient, it is incumbent that total spinal immobilization backboards be made of such rigid construction that even heavy adults (up to 300 pounds or more) can be supported and transported without substantial deviation (less than $\frac{1}{2}$ inch) in either a longitudinal or lateral direction. This necessity has heretofore required the use of reusable hard wood or metal boards.

While total spinal immobilization boards have had a positive impact in the medical rescue profession, along with the growth of these devices as valued aids has arisen several unattended and generally unrecognized shortfalls.

First, because it is the function of these boards to totally immobilize until an exact diagnosis can be obtained, it is most often necessary that the board stay attached through the patient's admission into the hospital, x-rays, and sometimes even through surgery. The actual board, however, is normally part of the standard issue equipment for a particular ambulance, which may on occasion require the use of that board again prior to the time when it would be expected to be returned. This logistical complication in the actual operating use of total spinal immobilization backboards has given rise to a practice of board borrowing, tracing, and returning which is, at least, inefficient, and occasionally has left EMT personnel in situations where a total spinal immobilization backboard is needed but is not at hand.

Secondly, disaster situations reveal both the need for, and insufficiency of, total spinal immobilization backboards as they now exist. Where there are a large number of casualties requiring immediate medical rescue, the readiness of both medical rescue personnel and medical rescue equipment is tested. Thus another shortfall of total spinal immobilization boards is that, even though they may be the preferred means of casualty transport, they are not readily available in sufficient quantities when the need for them may be the most. By the very nature of their expense (typically in the order of $100 ) these boards are not stocked in quantities necessary to accommodate the need in most disaster situations. As a result medical rescue personnel turn to other, less desired, ways of transporting many disaster victims to triage areas.

Moreover, the factors of cost and general lack of availability have helped to keep total spinal immobilization backboards from becoming generally known by, or generally accessible to, the general public. There are many occasions (swimming pools, boating situations, and generally any remote area situation) where the availability of a total spinal immobilization backboard may be put to the worthy use of preventing paralysis or death. Unfortunately, this has not been the case.

The present invention is intended to alleviate the above expressed concerns by providing a low cost, disposable total spinal immobilization backboard. These and other objects and advantages of the present invention will become apparent from a review of the following disclosure.

DESCRIPTION OF THE PREFERRED EMBODIMENT

Figure 1:
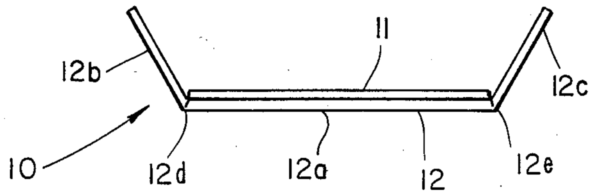
FIG. 1 is an end elevational view of a total spinal immobilization board according to the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring now to FIG. 1, this figure illustrates an end elevational view of a total spinal immobilization board 10 according to the present invention in an unused state. Total spinal immobilization board 10 includes a first panel member 11 and a second cradle member 12. Both panel 11 and cradle 12 are constructed of corrugated material which is impregnated with a parraffin based or polymeric waxing substance through a cascading process.

Cascading of the material acts both to waterproof total spinal immobilization board 10 and to improve the weight carrying ability of total spinal immobilization board 10 by increasing its rigidity and strength. Other waterproofing means, such as spraying, do not give the same effect of improving the weight carrying ability of the corrugated material. A cascaded corrugated material which provides the strength and rigidity for total spinal immobilization in the embodiment of FIGS. 1–4 is 1100 CAA triple flute fiberboard, with ply weights of 90, 42, 42, and 90 pounds/1000 sq. ft., and with a medium weight of 26 pounds/1000 sq. ft. For further measure, the fluting may be increased to AAA, the intermediate plys increased to 90 pounds/100 sq. ft., and the medium to 40 pounds/100 sq. ft. Further increases involve obtaining or constructing material which are considered to not be generally commercially available.

Cradle 12 includes panel portion **12*a*, folding portions 12*b* and 12*c*, and preformed folds 12*e* and 12*f*. Panel portion 12*a* is positioned immediately underneath, and laminated to, panel 11. Wing portions 12*b* and 12*c* pivotally connect with panel portion 12*a* at preformed folds 12*e* and 12*f*.**

Figure 2:
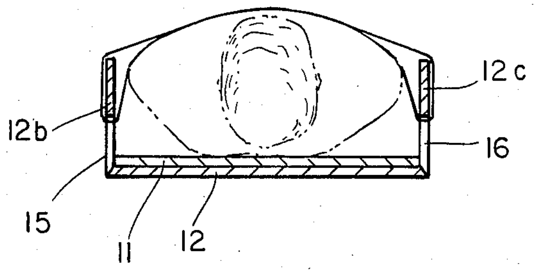
FIG. 2 is an end elevational view of the total spinal immobilization board of FIG. 1 onto which is placed and immobilized an injured person.
Figure 3:
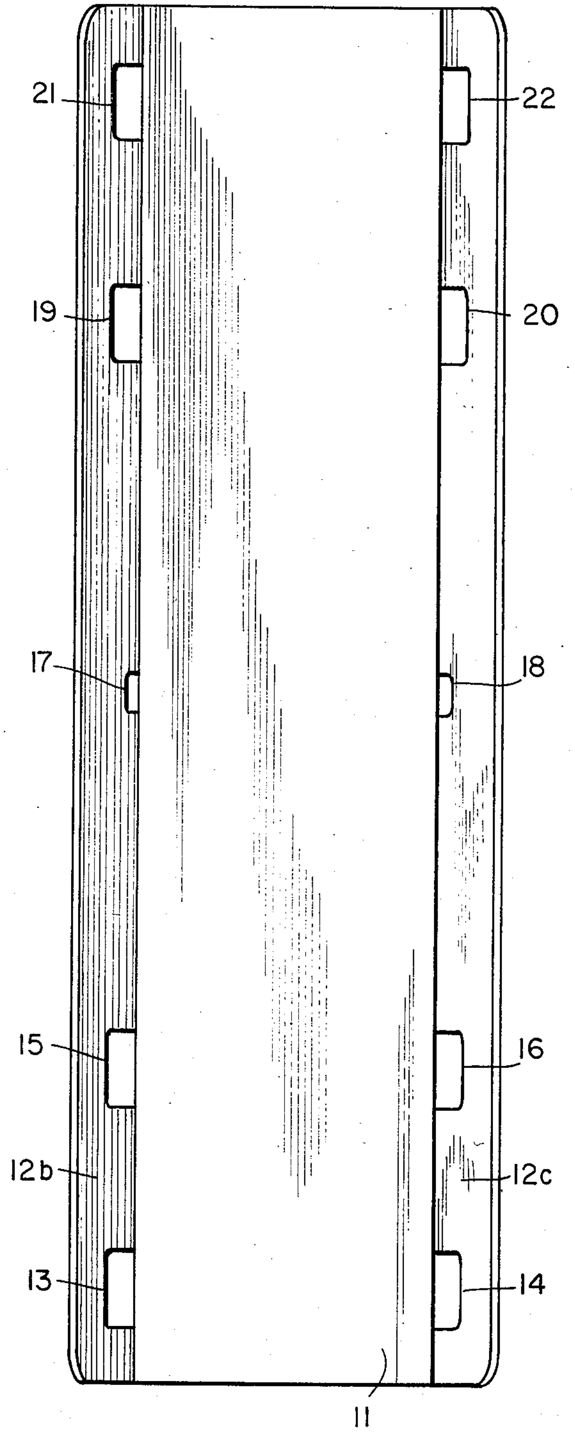
FIG. 3 is a top plan view of the total spinal immobilization board of FIG. 1.
Figure 4:
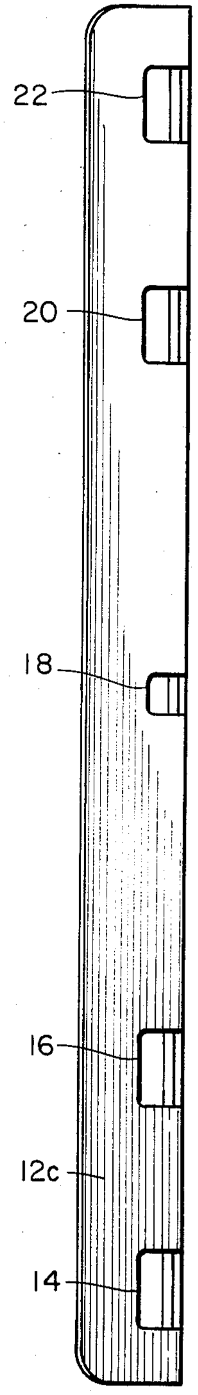
FIG. 4 is a side elevational view of the total spinal immobilization board of FIG. 1.

As may be seen from FIGS. 3 and 4, folding portions **12*b* and 12*c* define a series of corresponding holes 13 and 14, 15 and 16, 17 and 18, 19 and 20, and 21 and 22. Holes 13 and 14, 15 and 16, 19 and 20, and 21 and 22 are sized to receive hands for the carrying of said backboard in the transporting of an injured party. Holes 13 and 14, 15 and 16, 19 and 20, and 21 and 22 are also used for securedly accepting strapping material for the immobilizing strapping of an injured party to said disposable total spinal immobilization backboard (see FIG. 2). Additionally, holes 17 and 18 are sized only for accepting strapping material and not to receive hands. Holes 17 and 18 may also be positioned above, rather than along, preformed folding lines 12*e* and 12*f* respectively to improve the strength at these stress points. 2 ply polyester tape can be used as a suitable disposable strapping material which sufficiently immobilizes an injured person and can be disposed with board 10** after its one time use. Regular medical straps, or any other suitable strapping means which effectuate immobilization, are of course also usable with the present invention.

The allowed relative movement of the lumbar spine should be less than ½ inch, and an injury to the cervical spine can be aggravated by even less movement than that which would aggravate an injury to the lumbar area. The disposable total spinal immobilization backboard of FIGS. 1–4, as has thus far been described, when properly used, successfully immobilizes a patient for transport to this degree. With a person strapped into board 10, as shown in FIG. 2, a person of up to 300 pounds can be supported with less than ½ inch of deviation at the center of the board which supports the lumbar region. The extremely small fraction of people who are greater in weight can not be safely carried by only two people because of the tremendous load. In such instances, the load can be more evenly distributed, and thus the deviation lessened, by having additional people aid in the carrying.

There are a variety of ways in which an injured party may be securely immobilized to board 10. Also, while the present invention is a total spinal immobilization device, it is apparent that it can serve as a simple stretcher as well. It may be seen in FIG. 2 that by one method of strapping the injured party onto board 10, folding sections **12*b* and 12*c* are brought to an upright, or near upright, position. During the subsequent transfer, folds 12*d* and 12*e* thus contribute to the strength of board 10 to ensure immobilization whether board 10 is held by the handholds provided or whether it is held from underneath. Alternatively, though, the person may be strapped through handholds (15 and 16 of FIG. 2 for example) and around panel portion 12*a*, or may not be strapped at all when board 10 is used as a simple stretcher. In such instances, the device of FIGS. 1–4 must be lifted by means of the handholds provided to ensure the contribution to the strength of board 10** provided by folds 12*d* and 12*e*. Since this procedure can not always be relied upon, and in light of the severe consequences in the event that a board would break or weaken during transfer, the following further embodiment will now be described.

Figure 5:
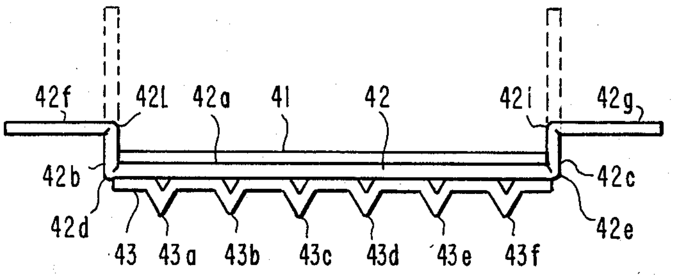
FIG. 5 is an end elevational view of a second embodiment of a total spinal immobilization board according to the present invention including a third ribbed layer of corrugated material.
Figure 6:
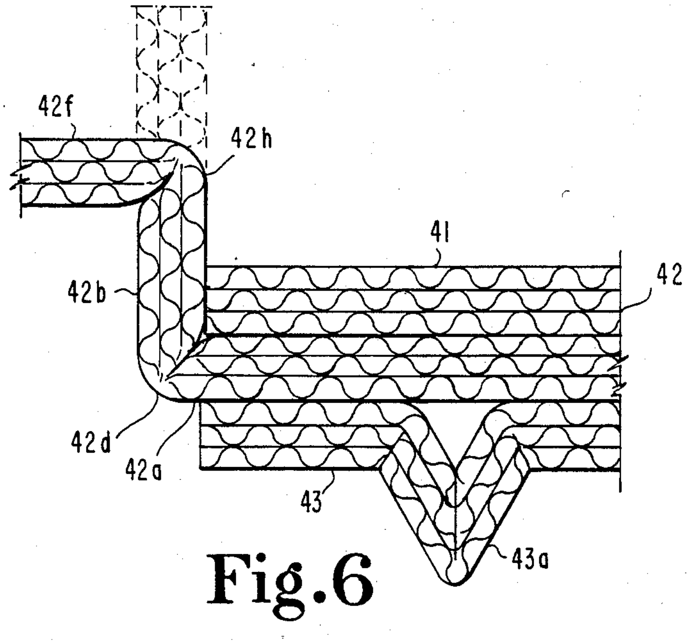
FIG. 6 is a fragmentary end elevational view of the folding joints of the total spinal immobilization board of FIG. 5.

FIGS. 5 and 6 disclose a second disposable total spinal immobilization board 40 according to the present invention. Except for the differences shown and described, board 40 is to be considered the same as board 10 in structure and design. Total spinal immobilization board 40 includes a first panel member 41, a second cradle member 42, and a third ribbed member 43 of corrugated material. Ribbed member 43 is laminated to cradle member 42 and includes a series of longitudinal ribs 43*a–f* formed by folds in member 43. Ribs 43*a–f* act to add longitudinal strength to board 40, also serve to raise board 40 slightly above the ground when it is placed down, and further facilitate sliding board 40 when moving board 40 by that means may be desired or necessary.

As opposed to folds 12*d* and 12*e* of board 10, preformed folds 42*d* and 42*e* are permanent and are not pivotable. Thus portions 42*b* and 42*c* are always maintained in an upright position and the structural support provided by board 40 is constantly maintained regardless of the manner by which the person is strapped or the way board 40 is carried. Additional preformed folds 42*h* and 42*i*, on the other hand, are pivotable, allowing wing portions 42*f* and 42*g* respectively, to pivot between the horizontal positions shown and upright positions (dashed lines). When positioned horizontally, wing portions 42*f* and 42*g* facilitate the transfer of a person onto board 40 (transfer techniques often require that a board be slid under the person or that he be carefully and delicately lifted and placed on the receiving board). After transfer onto board 40 is completed, wing portions may be raised and used for strapping to immobilize the injury as has been previously described with regard to board 10.

Additionally, it may be noted that wings 42*f* and 42*g* (and 12*b* and 12*c* for board 10) provide a measure of psychological security to the person being carried that is not given by conventional immobilization backboards. With conventional devices, the person carried often get the sensation that he is going to fall off. This is especially true since, with a conventional board, he most often can not even see what he has been strapped onto. This apprehension, though, is alleviated where some side structure is detectible. It is suggested, in jest, that perhaps this increased sense of security would be counterbalanced were the carryee to find out that he is being conveyed via cardboard.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A disposable total spinal immobilization backboard comprising a panel of multiple ply corrugated material, said multiple ply corrugated material being impregnated with a waxing substance causing said material to be waterproofed and increasing the rigidity and strength of said material; one ply of said panel including two permanent longitudinal fold lines, each of said permanent longitudinal fold lines connecting a central horizontal portion of said ply with one of two opposing vertical portions of said ply, said ply further including two pivotable longitudinal fold lines, each of said pivotable longitudinal fold lines connecting one of said opposing vertical portions with one of two opposing extending wing portions of said ply, said extending wing portions being pivotable between first horizontally extending positions to facilitate storage and transfer of a patient onto said backboard and second vertically extending positions to facilitate strapping of a patient to said backboard and transport of an injured party on said backboard, said panel being sized to be about as long as and about as wide as an average person when said extending wing portions are in said second vertically extending positions; said disposable total spinal immobilization backboard being reinforced both laterally and longitudinally to allow a deflection of less than ½ inch when supporting a body weight of 300 pounds; said disposable total spinal immobilization backboard further comprising handhold means for receiving hands for the carrying of said backboard in the transporting of an injured party, said disposable total spinal immobilization backboard further comprising strap receiving means for securedly accepting strapping material for the immobilizing strapping of an injured party to said disposable total spinal immobilization backboard.

2. A disposable total spinal immobilization backboard comprising a panel of multiple ply cascaded corrugated material, said multiple ply corrugated material being impregnated with a waxing substance by a cascading process causing said material to be waterproofed and increasing the rigidity and strength of said material; one ply of said panel including two permanent longitudinal fold lines, each of said permanent longitudinal fold lines connecting a central horizontal portion of said ply with one of two opposing vertical portions of said ply, said ply further including two pivotable longitudinal fold lines, each of said pivotable longitudinal fold lines connecting one of said opposing vertical portions with one of two opposing extending wing portions of said ply, said extending wing portions being pivotable between first horizontally extending positions to facilitate storage and transfer of a patient onto said backboard and second vertically extending positions to facilitate strapping of a patient to said backboard and transport of an injured party on said backboard, said panel being sized to be about as long as and about as wide as an average person when said extending wing portions are in said second vertically extending positions; said disposable total spinal immobilization backboard being reinforced both laterally and longitudinally to allow a deflection of less than ½ inch when supporting a body weight of 300 pounds; said disposable total spinal immobilization backboard further comprising handhold means for receiving hands for the carrying of said backboard in the transporting of an injured party, said disposable total spinal immobilization backboard further comprising strap receiving means for securedly accepting strapping material for the immobilizing strapping of an injured party to said disposable total spinal immobilization backboard.

3. A disposable total spinal immobilization backboard comprising a panel of multiple ply corrugated material, said multiple ply corrugated material being impregnated with a waxing substance causing said material to be waterproofed and increasing the rigidity and strength of said material; one ply of said panel including two permanent longitudinal fold lines, each of said permanent longitudinal fold lines connecting a central horizontal portion of said ply with one of two opposing vertical portions of said ply, said ply further including two pivotable longitudinal fold lines, each of said pivotable longitudinal fold lines connecting one of said opposing vertical portions with one of two opposing extending wing portions of said ply, said extending wing portions being pivotable between first horizontally extending positions to facilitate storage and transfer of a patient onto said backboard and second vertically extending positions to facilitate strapping of a patient to said backboard and transport of an injured part on said backboard, said panel having a width of less than 18 inches when said extending wing portions are in said second vertically extending positions and a length of about 6 feet; said disposable total spinal immobilization backboard being reinforced both laterally and longitudinally to allow a deflection of less than ½ inch when supporting a body weight of 300 pounds; said disposable total spinal immobilization backboard further comprising handhold means for receiving hands for the carrying of said backboard in the transporting of an injured party, said disposable total spinal immobilization backboard further comprising strap receiving means for securedly accepting strapping material for the immobilizing strapping of an injured party to said disposable total spinal immobilization backboard.

4. A disposable total spinal immobilization backboard comprising a panel of multiple ply corrugated material, said multiple ply corrugated material being impregnated with a waxing substance causing said material to be waterproofed and increasing the rigidity and strength of said material; one ply of said panel including two permanent longitudinal fold lines, each of said permanent longitudinal fold lines connecting a central horizontal portion of said ply with one of two opposing vertical portions of said ply, said ply further including two pivotable longitudinal fold lines, each of said pivotable longitudinal fold lines connecting one of said opposing vertical portions with one of two opposing extending wing portions of said ply, said extending wing portions being pivotable between first horizontally extending positions to facilitate storage and transfer of a patient onto said backboard and second vertically extending positions to facilitate strapping of a patient to said backboard and transport of an injured party on said backboard, said panel having a width of less than 18 inches when said extending wing portions are in said second vertically extending positions and a length of about 6 feet; said disposable total spinal immobilization backboard having at least six layers of body supporting corrugation and being further reinforced to allow a deflection of less than ½ inch either laterally or longitudinally when exposed to a body weight of 300 pounds; said disposable total spinal immobilization backboard further comprising handhold means for receiving hands for the carrying of said backboard in the transporting of an injured party, said disposable total spinal immobilization backboard further comprising strap receiving means for securedly accepting strapping material for the immobilizing strapping of an injured party to said disposable total spinal immobilization backboard.

5. A method for making a disposable total immobilization backboard comprising the steps of:

(1) constructing an immobilization backboard frame by
  (a) forming a panel of multiple ply corrugated material, one ply of the panel including two permanent longitudinal fold lines, each of the permanent longitudinal fold lines connecting a central horizontal portion of the ply with one of two opposing vertical portions of the ply, the ply further including two pivotable longitudinal fold lines, each of the pivotable longitudinal fold lines connecting one of the opposing vertical portions with one of two opposing extending wing portions of the ply, the extending wing portions being pivotable between first horizontally extending positions to facilitate storage and transfer of a patient onto the backboard and second vertically extending positions to facilitate strapping of a patient to the backboard and transport of an injured party on the backboard, the formed panel being sized to be about as long as and about as wide as an average person when the extending wing portions are in the second vertically extending positions, and
  (b) forming handholds and strapholds integrally connected to the formed panel; and
(2) cascading said constructed immobilization backboard with a waxing substance which impregnates the multiple ply corrugated material to both waterproof the constructed frame and increase the frame's strength and rigidity to enable the frame to allow a body weight of 300 pounds with a deflection of less than ½ inch either laterally or longitudinally.

6. A method for transporting an injured person comprising the steps of:

(1) placing the injured person in the position he has been found on a panel of multiple ply corrugated material one ply of the panel including two permanent longitudinal fold lines, each of the permanent longitudinal fold lines connecting a central horizontal portion of the ply with one of two opposing vertical portions of the ply, the ply further including two pivotable longitudinal fold lines, each of the pivotable longitudinal fold lines connecting one of the opposing vertical portions with one of two opposing extending wing portions of the ply, the extending wing portions being pivotable between first horizontally extending positions to facilitate storage and transfer of a patient onto the backboard and second vertically extending positions to facilitate strapping of a patient to the backboard and transport of an injured party on the backboard, the panel being sized to be about as long and about as wide as an average person when the extending wing portions are in the second vertically extending positions, the material having been cascaded with a paraffin based wax;
(2) placing the person in the position found onto the panel with the extending wing portions in horizontally extending positions;
(3) immobilizing the person in the position found to the panel by strapping him to the panel with the winged portions in vertically extending positions;
(4) transporting the person by carrying the panel; and
(5) disposing of the panel after a single use.

* * * * *